US011077072B2

(12) United States Patent
Golan

(10) Patent No.: US 11,077,072 B2
(45) Date of Patent: *Aug. 3, 2021

(54) BINGE BEHAVIOR REGULATORS

(71) Applicant: Ezekiel Golan, Vancouver (CA)

(72) Inventor: Ezekiel Golan, Vancouver (CA)

(73) Assignee: Clearmind Medicine Inc.

( * ) Notice: Subject to any disclaimer, the term of this patent is extended or adjusted under 35 U.S.C. 154(b) by 0 days.

This patent is subject to a terminal disclaimer.

(21) Appl. No.: 16/563,974

(22) Filed: Sep. 9, 2019

(65) Prior Publication Data
US 2020/0000747 A1 Jan. 2, 2020

Related U.S. Application Data

(63) Continuation of application No. 16/167,576, filed on Oct. 23, 2018, now Pat. No. 10,406,123, which is a continuation of application No. 15/534,137, filed as application No. PCT/IL2015/051193 on Dec. 9, 2015, now Pat. No. 10,137,096.

(60) Provisional application No. 62/089,500, filed on Dec. 9, 2014, provisional application No. 62/089,504, filed on Dec. 9, 2014.

(51) Int. Cl.
| A61K 31/135 | (2006.01) |
| A61P 25/30 | (2006.01) |
| A61P 25/32 | (2006.01) |
| A23L 2/52 | (2006.01) |
| A61K 31/255 | (2006.01) |
| A61K 31/357 | (2006.01) |
| A61K 31/36 | (2006.01) |
| A61K 31/40 | (2006.01) |
| C12C 5/02 | (2006.01) |

(52) U.S. Cl.
CPC .............. *A61K 31/135* (2013.01); *A23L 2/52* (2013.01); *A61K 31/255* (2013.01); *A61K 31/357* (2013.01); *A61K 31/36* (2013.01); *A61K 31/40* (2013.01); *A61P 25/30* (2018.01); *A61P 25/32* (2018.01); *C12C 5/02* (2013.01); *C12G 2200/21* (2013.01)

(58) Field of Classification Search
CPC .. A61K 31/135; A61K 31/255; A61K 31/357; A61K 31/36; A61K 31/40; A61P 25/30; A61P 25/32; A23L 2/52; C12C 5/02
USPC ........................................................ 514/657
See application file for complete search history.

(56) References Cited

U.S. PATENT DOCUMENTS

| 2,712,998 A | 7/1955 | Vosseler |
| 4,990,350 A | 2/1991 | Rohmann |
| 5,708,018 A * | 1/1998 | Haadsma-Svensson ..................... C07C 211/42 514/408 |
| 6,933,410 B2 | 8/2005 | Prashad et al. |
| 10,137,096 B2 * | 11/2018 | Golan .................. A61K 31/135 |
| 10,406,123 B2 * | 9/2019 | Golan .................. A61K 31/255 |
| 2010/0113512 A1 | 5/2010 | Ignar |
| 2012/0122823 A1 | 5/2012 | Reed |
| 2017/0360067 A1 | 12/2017 | Golan |
| 2018/0085326 A1 | 3/2018 | Golan |
| 2019/0054042 A1 | 2/2019 | Golan |

FOREIGN PATENT DOCUMENTS

| DE | 952441 | 11/1956 | |
| EP | 2556830 | 2/2013 | |
| WO | WO 95/04713 | 2/1995 | |
| WO | WO 99/14207 | 3/1999 | |
| WO | WO 99/19325 | 4/1999 | |
| WO | WO 01/34172 | 5/2001 | |
| WO | WO 02/064545 | 8/2002 | |
| WO | WO-2004037777 A1 * | 5/2004 | ........... C07C 275/34 |
| WO | WO 2006/015828 | 2/2006 | |
| WO | WO 2007/069925 | 6/2007 | |
| WO | WO 2009/125923 | 10/2009 | |
| WO | WO 2016/092546 | 6/2016 | |
| WO | WO 2016/092547 | 6/2016 | |

OTHER PUBLICATIONS

International Preliminary Report on Patentability dated Jun. 22, 2017 From the International Bureau of WIPO Re. Application No. PCT/IL2015/051193. (8 Pages).
International Preliminary Report on Patentability dated Jun. 22, 2017 From the International Bureau of WIPO Re. Application No. PCT/IL2015/051194. (8 Pages).
International Search Report and the Written Opinion dated Apr. 4, 2016 From the International Searching Authority Re. Application No. PCT/IL2015/051193.
International Search Report and the Written Opinion dated Mar. 22, 2016 From the International Searching Authority Re. Application No. PCT/IL2015/051194.
Notice of Allowance dated Jul. 20, 2018 From the US Patent and Trademark Office Re. U.S. Appl. No. 15/534,137. (7 pages).
Notification of Office Action and Search Report dated Dec. 20, 2018 From the National Intellectual Property Administration of the People's Republic of China Re. Application No. 201580075683.X and Its Summary in English. (13 Pages).
Notification of Office Action and Search Report dated Dec. 20, 2018 From the State Intellectual Property Office of the People's Republic of China Re. Application No. 201580075677.4 and Its Summary in English. (12 Pages).
Notification of Office Action dated Aug. 21, 2019 From the National Intellectual Property Administration of the People's Republic of China Re. Application No. 201580075677.4 and Its Translation Into English. (17 Pages).

(Continued)

*Primary Examiner* — Yevgeny Valenrod
(74) *Attorney, Agent, or Firm* — Finnegan, Henderson, Farabow, Garrett & Dunner, LLP

(57) ABSTRACT

Methods and compositions utilizing 2-aminoindan derivatives collectively represented by Formula I as described and defined in the specification for regulating binge behavior, particularly binge drinking, are disclosed.

13 Claims, No Drawings

(56) References Cited

OTHER PUBLICATIONS

Notification of Office Action dated Aug. 21, 2019 From the National Intellectual Property Administration of the People's Republic of China Re. Application No. 201580075683.X and Its Translation Into English. (15 Pages).
Official Action dated Dec. 11, 2018 From the US Patent and Trademark Office Re. U.S. Appl. No. 16/167,576. (13 pages).
Official Action dated Mar. 14, 2018 From the US Patent and Trademark Office Re. U.S. Appl. No. 15/534,137. (13 pages).
Official Action dated Apr. 26, 2018 From the US Patent and Trademark Office Re. U.S. Appl. No. 15/534,121. (14 pages).
Official Action dated Feb. 27, 2019 From the US Patent and Trademark Office Re. U.S. Appl. No. 15/534,121. (24 pages).
Restriction Official Action dated Feb. 1, 2018 From the US Patent and Trademark Office Re. U.S. Appl. No. 15/534,121. (14 pages).
Supplementary European Search Report and the European Search Opinion dated Jul. 2, 2018 From the European Patent Office Re. Application No. 15867070.3. (11 Pages).
Supplementary European Search Report and the European Search Opinion dated Jul. 2, 2018 From the European Patent Office Re. Application No. 15867972.0. (8 Pages).
Akincioglu et al. "Novel Sulfamides as Potential Carbonic Anhydrase Isoenzymes Inhibitors", Bioorganic & Medicinal Chemistry, 21(6): 1379-1385, Available Online Jan. 22, 2013.
Anton et al. "Combined Pharmacotherapies and Behavioral Interventions for Alcohol Dependence", Journal of the American Medical Association, JAMA, 295(17): 2003-2017, May 3, 2006.
Arneric et al. "Potent Anorexic-Like Effects of RDS-127 (2-Di-N-Propylamino-4, 7-Dimethoxyindane) in the Rat: A Comparison With Other Dopamine-Receptor Agonists", Neuropharmacology, XP025559703, 21(9), 885-890, Sep. 1, 1982.
Bluelight "5-Meo-A1", Bluelight, 6 P., Dec. 31, 2014.
Boyce et al. "Enhancement of Ethanol Reward by Dopamine D3 Receptor Blockade", Brnn Rasearch, 88(1): 202-206, Aug. 2, 2000.
Brandt et al. "Aminoindane Analogues", Novel Psychoactive Substances, Academic Press, pp. 261-283, Jan. 1, 2013.
Burn-Callander et al. "Get Drunk Without a Hangover on Synthetic Booze", Telegraph Media Group, 4 P., Jan. 22, 2015.
Chick et al. "Substitution Therapy for Alcoholism: Time for A Reappraisal?", Journal of Psychopharmacology, 26(2): 205-212, Published Online Jul. 8, 2011.
Fisher "Doctors Have Discovered the Simplest Way to Quit Drinking—by Doing Drugs", Mic, 2 P., Jan. 8, 2015.
Giuliano et al. "Attenuation of Cocaine and Heroin Seeking by [mu]-opioid Receptor Antagonism", Psychopharmacology, XP035370001, 227(1): 137-147, Published Online Jan. 9, 2013.
Gray "Could A Legal High That Mimics Ecstasy Stop People From Boozing? Party Drug Is Patented for Use as 'Binge Mitigation Agent'", Daily Mail Online, 16 P., Dec. 31, 2014.
Haadsma-Svensson et al. "Dopamine D3 Receptor Antagonists.I. Synthesis and Structure-Activity Relationships of 5,6-Dimethoxy-N-Alkyl- and N-Alkylaryl-Substituted 2-Aminoindans", The Journal of Medicinal Chemistry, 44(26): 4716-4732, Published on Web Nov. 17, 2001.
Heidbreder et al. "Role of Dopamine D3 Receptors in the Addictive Properties of Ethanol", Drugs of Today, 40(4): 355-365, 2004.
Johnson "Progress in the Development of Topiramate for Treating Alcohol Dependence: From A Hypthesis to a Proof-of-Concept Study", Alcoholism: Clinical and Experimental Research, 28(8): 1137-1144, Aug. 2004.
Karhuvaara et al. "Targeted Nalmefene With Simple Medical Management in the Treatment of Heavy Drinkers: A Randomized Double-Blind Placebo-Controlled Multicenter Study", Alcolholism: Clinical and Experimental Research, 31(7): 1179-1187, Jul. 2007.
Kelly et al. "The Opioid Receptor Pharmacology of GSK1521498 Compared to Other Ligands With Differential Effects on Compulsive Reward-related Behaviours", Psychopharmacology, XP035416399, 232(1): 305-314, Published Online Jun. 29, 2014.
Koob "Alcoholism: Allostasis and Beyond", Alcoholism: Clinical and Experimental Research, 27(2): 232-243, Feb. 2003.
Lingford-Hughes et al. "Neuropharmacology of Addiction and How It Informs Treatment", British Medical Bulletin, 96: 93-110, Published Online Nov. 2, 2010.
Nutt "Alcohol Without the Hangover? It's Closer Than You Think", The Guardian, 2 P., Nov. 11, 2013.
Nutt et al. "Through A Glass Darkly: Can We Improve Clarity About Mechanism and Aims of Medications in Drug and Alcohol Treatments'?", Journal of Physchopharmacology, 26(2): 199-204, Feb. 2012.
Roesner et al. "Acamprosate Supports Abstinence, Naltrexone Prevents Excessive Drinking: Evidence From a Meta-Analysis With Unreported Outcomes", Journal of Psychopharmacology, 22(1): 11-23, Jan. 2008.
Skett "Care for a Legal Hight That's 'Chaperon-ed by Imperial'? New Party Drug Currently Being Developed by Nutt's Team Could Stop Binge Drinking But Still Deliver A High", News—Felix Online, 5 P., Jan. 16, 2015.
Slezak "High and Dry? Party Drug Could Target Excess Drinking. A Patent Has Been Filed for a Drug That Produces Some of Ecstasy's Euphoric Effects—and Seems to Put the Brakes on Boozing", New Scientist, 5 P., Dec. 30, 2014.
Traits "How Safe Are My Drugs?", BBC Three, 3 P., Jan. 29, 2015.
Vengeliene et al. "The Dopamine D3 Receptor Plays an Essential Role in Alcohol-Seeking and Relapse", The FASEB Journal, 20(13): 2223-2233, Jan. 1, 2006.
Weiss et al. "Behavioral Neurobiology of Alcohol Addiction: Recent Advances and Challenges", The Journal of Neuroscience, 22(9): 3332-3337, May 1, 2002.
Wikipedia "MEAL", Wikipedia, the Free Encyclopedia, 2 P., Last Modified Dec. 13, 2015.
Ziauddeen et al. "Effects of the Mu-opioid Receptor Antagonist GSK1521498 on Hedonic and Consummatory Eating Behaviour: A Proof of Mechanism Study in Binge-Eating Obese Subjects", Molecular Psychiatry, XP9506312, 18(12): 12871293, Published Online Nov. 13, 2012. p. 1288, col. 2, Para [0001], p. 1292.
Decision on Rejection dated Mar. 26 2020 From the National Intellectual Property Administration of the People's Republic of China Re. Application No. 201580075683.X and its Translation Into English (14 Pages).
Decision on Rejection dated Mar. 26, 2020 From the National Intellectual Property Administration of the People's Republic of China Re. Application No. 201580075683.X and Its Translation Into English. (24 Pages).
Official Action dated May 21, 2020 from the US Patent and Trademark Office Re. U.S. Appl. No. 15/534,121. (14 pages).
Final Official Action dated Feb. 3, 2021 From the US Patent and Trademark Office Re. U.S. Appl. No. 15/534,121. (16 Pages).
Examination Report Under Sections 12 & 13 of the Patents Act, 1970 and the Patents Rules, 2003 dated Dec. 24, 2019 From the Government of India, Intellectual Property India, Patents, Designs, Trade Marks, Geographical Indications, The Patent Office Re. Application No. 201727023745. (7 Pages).
Examination Report Under Sections 12 & 13 of the Patents Act, 1970 and the Patents Rules, 2003 dated Nov. 7, 2020 From the Government of India, The Patent Office, Intellectual Property India, Patents, Designs, Trade Marks, Geographical Indications Re. Application No. 201727023744. (6 Pages).
Examination Report Under Sections 12 & 13 of the Patents Act, 1970 and the Patents Rules, 2003 dated Nov. 7, 2019 From the Government of India, The Patent Office, Intellectual Property India, Patents, Designs, Trade Marks, Geographical Indications Re. Application No. 201727023744. (6 Pages).
Official Action dated Oct. 29, 2019 From the US Patent and Trademark Office Re. U.S. Appl. No. 15/534,121. (18 Pages).
Applicant-Initiated Interview Summary dated Feb. 26, 2020 From the US Patent and Trademark Office Re. U.S. Appl. No. 15/534,121. (3 pages).
European Search Report and the European Search Opinion dated Aug. 12, 2020 From the European Patent Office Re. Application No. 20161755.2. (14 Pages).

(56) References Cited

OTHER PUBLICATIONS

Akbaba et al. "Synthesis and Asymmetric Resolution of A Dopaminergic Compound: 2-Amino-5-Methoxyindane", Tetrahedron Asymmetry, XP029554246, 27(11): 475-479, Available Online Apr. 28, 2016.
Shimshoni et al. "Toxicological Evaluation of 5-Methoxy-2-Aminoindane (MEAI): Binge Mitigating Agent in Development", Toxicology and Applied Pharmacology, XP029927268, 319: 59-68, Available Online Feb. 4, 2017.

* cited by examiner

BINGE BEHAVIOR REGULATORS

RELATED APPLICATIONS

This application is a continuation of U.S. patent application Ser. No. 16/167,576 filed on Oct. 23, 2018, which is a continuation of U.S. patent application Ser. No. 15/534,137 filed on Jun. 8, 2017, now U.S. Pat. No. 10,137,096, which is a National Phase of PCT Patent Application No. PCT/IL2015/051193 having International Filing Date of Dec. 9, 2015, which claims the benefit of priority under 35 USC § 119(e) of U.S. Provisional Patent Application Nos. 62/089,500 filed on Dec. 9, 2014 and 62/089,504 filed on Dec. 9, 2014.

The contents of the above applications are all incorporated by reference as if fully set forth herein in their entirety.

FIELD AND BACKGROUND OF THE INVENTION

The present invention, in some embodiments thereof, relates to binge behavior, and more particularly, but not exclusively, to compositions and methods for regulation of binge behavior such as binge drinking.

Binging or binge behavior is a non-controlled excessive behavior of indulgence in a variety of activities such as eating, drinking, drugs, sweets, shopping, sexual conduct, and the like. It is now recognized that all types of binging are ways of dealing with negative emotions that are not rational or healthy.

Binge disorders are characterized by feelings of powerlessness, secrecy, shame, and social isolation. The occasional overindulgence becomes a real problem once a subject feels a need to binge in private, or schedule binges around (or instead of) work and social obligations. Binge eating is currently the most common eating disorder in adults, compulsive buying disorder ("shopaholism") is increasing, and binge drinking is widespread.

The causes of any type of binge behavior can fall into three categories: psychological, chemical, and sociocultural.

Most common psychological causes of binging are anxiety, stress, and depression. While often binging is simply a way to numb unhappy feelings, it can also be a symptom of an undiagnosed mental disorder. Depression, for example, can lead to low self-esteem, body dissatisfaction, poor impulse control, and difficulty in managing feelings—all of which can trigger a binge. Naturally the pain and guilt that comes in the aftermath of a binge can trigger depression, which can trigger another binge, and so on.

The brain releases dopamine (DA) when eating fat and sugar, when drinking alcohol, or even when observing new things to buy. Once the brain secretes DA during binges, binges can become like a physical addiction—one binges more and more because one craves the rush of chemicals. Similarly, low levels of DA and serotonin can lead to compulsive behavior (like bingeing) and depression.

Stress and anxiety can also make people binge by making them more prone to "reward seeking behavior". Basically stress can cause loss of perspective and prioritizing the nice feelings ("reward") one gets during a binge over the regret that inevitably comes later.

Sociocultural circumstances, such as the pressures of a culture that emphasizes "coolness" through consumption, on a background of a poor sense of self-confidence, can also drive people to binges. The pressure to be perfect most often leads to anxiety and binge-like behavior.

First steps that may be taken by a person engaged in binge behavior, herein also referred to as a "binger", in order to regulate binge behavior and reduce the harmful effects thereof, include, for example, visiting a cognitive behavioral therapist and/or controlling binges through continued therapy. Support groups like Alcoholics Anonymous, Overeaters Anonymous, or Debtors Anonymous are useful in many cases. In serious cases of binge behavior, namely to the point where it causes distress or financial, social, or physical harm, drug therapy is considered.

Alcohol is one of the favorite, commonly used, yet most dangerous psychoactive substances that may lead to binge behavior upon excessive, uncontrolled consumption. Alcohol is consumed for several reasons, which include quenching thirst, heating or cooling the drinker, for the taste and because of the association alcoholic drinks have with other aspects of life such as food and friendship. The psychological effects of alcohol contribute to some of these reasons.

Many people with alcohol dependence find that sometimes they can control their intake and have just a couple of drinks. Whereas at other times, even though they set out with the intention of only having a couple of drinks, they lose control once they have had the first drink and then take much more than they wanted to. Often this is in the form of a binge or 'bender'.

Alcohol consumption presents a growing problem worldwide, which some believe may have already overtaken tobacco in terms of overall health and social care costs. Excessive and/or prolonged alcohol consumption may have some undesired physiological and psychological, including short-term, effects such as gastric irritation, anxiety disorders and other excitable states, and longer-term effects such as cirrhosis, fatty liver disease, cardiomyopathy and dementia. Alcohol consumption may lead to intoxication, which, in turn, can have serious consequences such as accidents and uncontrolled violent behavior with subsequent medical complications.

The toxic element in alcohol is ethanol, a two-carbon chain alcohol that has a complex pharmacology. One of the current approaches to reduce or abolish the undesired effects of ethanol is to reduce the concentration of alcohol in drinks, by means of, for example, dealcoholized beverages such as dealcoholized beer and wine.

Neuroscientific advances have greatly increased the understanding of the pharmaco-behavioral effects of various neurotransmitter systems in the acquisition and maintenance of binge behavior in general and alcohol dependence, in particular.

Ethanol is a pluripotent drug that affects many neurotransmitter systems. The sedative, ataxic and eventually terminal anaesthetic actions of ethanol are thought to be mediated by interactions with primary amino acid ionotropic receptors, especially $GABA_A$ and glutamate receptors. Its major effect is on the endogenous inhibitory effect of the neurotransmitter γ-amino-butyric acid (GABA) by acting as an indirect agonist at the $GABA_A$ receptor [Nutt, Br J Psychiatry 175: 114-119, 1999], and possibly also the $GABA_B$ receptor. Midbrain and cortical dopamine (DA) pathways mediate alcohol's rewarding effects. Thus, while alcohol consumption increases GABA receptor activity, midbrain DA neurons are inhibited and DA neurotransmission is facilitated.

Alcohol is also an antagonist of the Non-N-methyl-D-aspartate (NMDA) type of glutamate receptors and hence reduces excitation in the central nervous system. NMDA glutamate antagonists oppose GABA activity, thereby decreasing DA release. These actions explain many of the effects of alcohol including its sedative, anxiolytic, amnestic and disinhibiting actions. Compensatory adaptive changes in these GABA and DA systems lead to a hyperexcitable state when alcohol intake is stopped, which explains many of the symptoms of withdrawal. The pleasurable effects associated with alcohol consumption as well as development and maintenance of alcohol dependence are attributed, at least in part, to these interactions, but are assumed to also involve interactions with endogenous opioids (i.e., beta-endorphin), serotonin (5-HT), and other amine systems.

In general, there are three types of treatments for addiction/dependence on alcohol and/or drugs: withdrawal treatment, substitution therapy and abstinence-promoting therapy [Nutt et al. J. Psychopharmacol. 2012, Vol. 26, No. 2, pp. 205-212].

The context of withdrawal treatment may vary, being sometimes elective (as a prior step in a patient's abstinence oriented therapy) or urgent, when some crisis has precipitated cessation of the addictive substance. Withdrawal reaction, if severe, might be life-threatening, as in severe alcohol addiction.

Substitution therapy is defined as utilizing a substituting agent (i.e., medication) that has one or more of the pharmacological effects of alcohol, which are believed to be relevant to the addiction. Substituting agents are generally effective in assisting withdrawal from alcohol abuse as they reduce craving and the desire to use alcohol. In many cases alcohol substitution therapy can be started once a decision is made to stop consuming alcohol.

An important group of agents useful in substitution therapy for alcohol dependence are drugs that potentiate the actions of GABA, thereby mimicking the actions of alcohol and substituting for it in withdrawal.

Such drugs include, for example, benzodiazepines, clomethiazole (a sedative and hypnotic agent), tiagabine, vigabatrin (both are anticonvulsants), oxybate or baclofen, which target the GABAergic system. These drugs affect the $GABA_A$ or $GABA_B$ receptors either directly (e.g., clomethiazole and baclofen), or indirectly (e.g., tiagabine that elevates GABA levels acutely by inhibiting GABA reuptake, or vigabatrin that elevates GABA levels chronically by irreversibly inhibiting catabolism of GABA via inhibition of GABA transaminase).

Currently known substitution treatment is such that can substitute for alcohol but cannot be used along with alcohol. Some of the alcohol substitution agents, particularly the $GABA_B$ receptors agonists, might have harmful effects when consumed together with alcohol (e.g. excessive sedation). This poses a severe limitation on the substitution treatment. A further concern associated with use of alcohol substitutents is development of dependence on these medications.

Abstinence promotion is the most widely recognized goal for addiction treatment. In the strict sense, abstinence refers to not taking the substance of abuse, nor taking substituting treatments. Abstinence promotion can be achieved, for example, by aversion.

Aversion is a long-established treatment for alcohol addiction. This treatment methodology is based on blocking alcohol metabolism to thereby lead to accumulation of metabolic intermediates. This methodology utilizes drugs such as disulfiram (Antabuse) and carbimide (Abstem), which are irreversible inhibitors of aldehyde dehydrogenase, and as such their administration results in accumulation of acetaldehyde (a toxic intermediate in alcohol metabolism) when alcohol is consumed. Acetaldehyde accumulation is highly unpleasant, cause nausea and/or vomiting, headache and flushing. The concept behind the use of drugs such as disulfiram is that the alcohol-dependent individual associates drinking with unpleasant adverse events. These adverse effects are intended to be off-putting and scary such that the alcoholic person is forced to refrain from drinking.

Anti-relapse drugs such as acamprosate, naltrexone, topiramate and gabapentin promote abstinence and reduce relapse risk through various mechanisms. Acamprosate, a structural analogue of GABA, increases abstinence rates and reduces the amount drunk in a lapse probably by attenuating conditioned responses to alcohol cues [Lingford-Hughes et al., Br Med Bull 96: 93-110, 2010]. Naltrexone (17-(cyclopropylmethyl)-4,5a-epoxy-3,14-dihydroxymorphinan-6-one hydrochloride), an opioid antagonist, blocks the reinforcing effects of alcohol by decreasing DA release in the nucleus accumbens, thus reducing craving and heavy drinking, and increasing the percentage of non-drinking days, however, not necessarily enhancing abstinence. Topiramate (2,3:4,5-bis-O-(1-methylethylidene)-beta-D-fructopyranose sulfamate), a GABA/glutamate modulator, is thought to have multiple mechanisms of action, amongst which is enhanced GABA inhibition that results in decreased DA facilitation in the midbrain [Johnson, 2004, Alcohol. Clin. Exp. Res., 28:1137-1144]. Gabapentin reduces glutamate and increases GABA neurotransmission in the brain. Theoretically, therefore, the unique pharmacology of these medications is well suited to the treatment of alcohol dependence or withdrawal and could normalize the brain dysregulation seen during the early abstinence period.

Dopamine receptors (DRs) are a class of G protein-coupled receptors that are prominent in the central nervous system (CNS). Dopamine receptors are implicated in many neurological processes, including motivation, pleasure, cognition, memory, learning, and fine motor control, as well as modulation of neuroendocrine signaling. Abnormal dopamine receptor signaling and dopaminergic nerve function is implicated in several neuropsychiatric disorders. Thus, dopamine receptors are common neurologic drug targets. Antipsychotics are often DRs antagonists, while psychostimulants are typically indirect agonists of DRs. It is believed that fluctuating dopamine (DA) levels contribute to craving, which leads in turn to relapse in abstinent alcoholics.

Antipsychotics (e.g., neuroleptics) that regulate DA occupancy at DRD2/DRD3, possibly causing an up-regulation of these receptors, have been hypothesized as associated with reduced positive symptoms of schizophrenia as well as reduced alcohol craving. The antipsychotics drugs haloperidol, tiapride, olanzapine, clozapine and aripiprazole have all demonstrated various degrees of efficacy in reducing craving and alcohol consumption or increasing abstinence. However, the risks associated with the side effects of typical or atypical neuroleptics have outweighed the benefits for using DA antagonists as a treatment of alcoholism.

Compounds derived from 2-aminoindan have been shown to selectively bind to the dopamine D3 receptor. U.S. Pat. No. 5,708,018 discloses some 2-aminoindan derivatives, and hypothesizes that these 2-aminoindan derivatives may be useful in treating CNS disorders associated with dopamine D3 receptor.

Various types of combination therapies have been used in an attempt to treat and prevent excessive alcohol drinking and dependence thereon. For example, European (EP) Patent No. 2556830 discloses combination therapy for the treatment of addictive use of alcohol and increase of abstinence rate, comprising the use of at least two anti-alcohol drugs such as topiramate, naltrexone and/or ondansetron (9-methyl-3-[(2-methyl-1H-inudazol-1-yl)methyl]-1,2,3,9-tetrahydrocarbazol-4-one), for reducing the frequency of alcohol consumption or the quantity of alcohol consumed. Anton et al. [2006, J. Am. Med. Assoc., 295:2003-2017] teaches combined pharmacotherapies (naltrexone and acamprosate) with behavioral therapy. However, current evidence for the usefulness of combination pharmacotherapy is lacking.

Harm reduction relates to new approaches (available or under investigation) that do not fall easily into current terminology, and include any intervention that reduces the harms of drugs/alcohol use, including social measures and medications.

In alcohol consumption, and particularly in excessive intake and alcohol dependence, the harm reduction approach is aimed at reducing harmful levels of drinking mainly by the use of drugs that reduce the amount of alcohol drunk in a single drinking session, and possibly the number of drinking sessions [Nutt et al. J. Psychopharmacol. 2012. Vol. 26. No. 2, pp. 205-212]. Harm reduction is thus obtained by the use of drink-regulating agents, also termed herein and in the art as binge regulators, drinking regulators, drinking restrictors, drinking-control agents, anti-bingeing agents or self-control drugs [Nutt et al. J. Psychopharmacol, 2012, Vol. 26, No. 2, pp. 205-212].

The feasibility of interfering with the destructive pattern of binge drinking came from studies with the opioid antagonists naltrexone and nalmefene when being used as part of a relapse prevention abstinence program. It was found that when used to assist abstinence, naltrexone, instead, was more effective at preventing a lapse becoming a full relapse, than in promoting complete abstinence [Rosner et al., J. Psychopharmacol 22: 11-23, 2008]. The mechanism seems to relate to endorphin: an important initial action of alcohol is to release endorphins, which then drive the dependence-prone person to drink more and more alcohol—so called loss-of-control drinking. Naltrexone and nalmefene block the endorphin effects and so lessen the risk of the drinking being leading to relapse. It was hypothesized that in this way these drugs lead to a lower, more regulated level of drinking with fewer binges/benders. When taken in a targeted (as required) fashion, that is, only on those days when the patient felt at risk of drinking, these drugs substantially reduced drinking than when taken each day [Karhuvaara et al., Alcohol Clin Exp Res 31: 1179-1187, 2007].

Nalmefene is marketed in Europe under the trade name Selincro. The UK National Institute for Health and Care Excellence (Nice) recommended the drug's use after trials showed it cut drinking by 61% over six months when used with counseling.

Nalmefene is administered orally as a pill once a day and is taken when people feel the urge to drink. It works by blocking the endorphin effects which gives drinkers pleasure from alcohol, stopping them from wanting more than one drink. Men would qualify to receive the treatment if they consume 7.5 units of alcohol per day (around three to four pints of standard strength lager (beer)), and women would qualify if they consume five units of alcohol a day, which amounts to around half a bottle of wine.

Nalmefene is now the only licensed medication which is aimed at reducing drinking rather than totally refrain from drinking. However, severe alcoholics and those who are not recognized as alcoholics or even as binger, are not eligible for the drug. Moreover, nalmefene cannot be consumed together with alcohol.

Additional Background art includes Koob, 2003, Alcohol Clin. Exp. Res., 27:232-243; and Weiss and Porrino, 2002, J. Neurosci., 22:3332-3337.

SUMMARY OF THE INVENTION

The need for binge regulation, such as regulation of alcoholic binging is yet unmet.

The idea that drugs might control or regulate binge behavior is a relatively new approach.

Binge regulators such as regulators of binge drinking present an alternative strategy to abstinence-promotion and target a group of alcohol-dependent patients who often are not interested in abstinence but rather are in need of better control on their alcohol consumption.

The present invention discloses compositions comprising a derivative of 2-aminoindan, as described herein, useful as binge regulators or binge mitigation agents that impart a feeling of satisfaction, satiety or contentedness and thereby regulate (e.g., discourage) binge behavior such as binge drinking.

According to an aspect of some embodiments of the present invention there is provided a method of regulating binge behavior, the method comprising administering to a subject in need thereof a compound represented by Formula I:

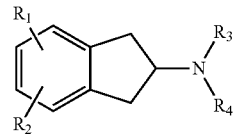

Formula I wherein:

each of $R_1$ and $R_2$ is independently selected from the group consisting of H, $(C_1-C_8)$alkyl, $(C_2-C_4)$alkenyl, $(C_2-C_8)$alkynyl, $(C_3-C_8)$cycloalkyl, aryl, heteroaryl, heteroalicyclic, —O$(C_1-C_6)$alkyl, OH, —OS(=O)$_2$CF$_3$, —OS(=O)$_2$—$(C_1-C_6)$alkyl, —S(=O)R$_5$, —CO$_2$R$_5$, —CONR$_5$R$_6$, —COR$_5$, —CF$_3$, CN, —SRS, —SO$_2$NR$_5$R$_6$, —SO$_2$R$_5$, —OCO—$(C_1-C_6)$alkyl, —NCO—$(C_1-C_6)$alkyl, —CH$_2$O—$(C_1-C_6)$alkyl, —$(C_1-C_6)$alkyl-OH, and halogen, or, alternatively, $R_1$ and $R_2$ together with two or more of the phenyl carbon atoms form a $X_1$—$(CR_5R_6)_m$—$X_2$— ring, wherein each of $X_1$ and $X_2$ is independently selected from O, NH or S and m is 1, 2, 3, or 4;

each of $R_3$ and $R_4$ is independently selected from the group consisting of H, $(C_1-C_8)$alkyl, $(C_2-C_8)$alkenyl, $(C_2-C_8)$alkynyl, $(C_3-C_8)$ cycloalkyl, and —$(CH_2)_p$-thienyl, wherein p is 1, 2, 3, or 4, or alternatively, $R_3$ and $R_4$ are joined together to form a heterocyclic ring (heteroalicyclic or heteroaryl) containing the nitrogen atom to which they are attached; and each of $R_5$ and $R_6$ is independently selected from the group consisting of H, $(C_1-C_8)$alkyl, $(C_2-C_8)$alkenyl, $(C_3-C_8)$cycloalkyl and aryl, thereby regulating the binge behavior.

According to an aspect of some embodiments of the present invention there is provided a compound represented by Formula I, as described herein in any one of the respective embodiments, for use in regulating binge behavior.

According to an aspect of some embodiments of the present invention there is provided a use of a compound represented by Formula I, as described herein in any one of the respective embodiments, for the preparation of a medicament for regulating binge behavior.

According to some of any of the embodiments of the present invention, the binge behavior is associated with alcohol consumption, eating, smoking, shopping or sexual conduct.

According to some of any of the embodiments of the present invention, the binge behavior is binge drinking.

According to an aspect of some embodiments of the present invention there is provided a method of regulating consumption of an alcoholic beverage, the method comprising administering to a subject in need thereof a compound represented by Formula I, or a composition comprising same, as described herein in any one of the respective embodiments, thereby regulating the consumption of an alcoholic beverage.

According to an aspect of some embodiments of the present invention there is provided a compound represented by Formula I, as described herein in any one of the respective embodiments, for use in regulating consumption of an alcoholic beverage.

According to an aspect of some embodiments of the present invention there is provided a use of a compound represented by Formula I, as described herein in any one of the respective embodiments, in the preparation of a medicament for regulating consumption of an alcoholic beverage.

According to some of any of the embodiments of the present invention, the consumption of alcoholic beverage is associated with binge drinking.

According to some of any of the embodiments of the present invention, the method or compound or use is for reducing an amount of alcohol consumption during a drinking session.

According to some of any of the embodiments of the present invention, the compound or the composition is administered before, simultaneously with, or subsequent to consumption of an alcoholic beverage.

According to some of any of the embodiments of the present invention, the compound is administered simultaneously with an alcoholic beverage.

According to some of any of the embodiments of the present invention, the compound is being incorporated in the alcoholic beverage.

According to some of any of the embodiments of the present invention, the amount of the compound is in the range selected from 0.15 mg/ml to 0.60 mg/ml, 0.15 mg/ml to 0.50 mg/ml, 0.15 to 0.40 mg/ml, 0.18 to 0.50 mg/ml, 0.18 to 0.40 mg/ml, 0.20 to 0.40 mg/ml, 0.20 to 0.30 mg/ml, 0.20 to 0.25 mg/ml, or 0.20 to 0.23 mg/ml.

According to some of any of the embodiments of the present invention, for a compound represented by Formula I, each of $R_1$ and $R_2$, each independently is selected from the group consisting of H, $(C_1$-$C_8)$alkyl, $(C_2$-$C_8)$alkenyl, $(C_2$-$C_8)$alkynyl, $(C_3$-$C_8)$cycloalkyl, aryl, —$OCH_3$, OH, —$OSO_2CF_3$, —$OSO_2CH_3$, —$SOR_5$, —$CO_2R_5$, —$CONR_5R_6$, —$COR_5$, —$CF_3$, —CN, —$SRS$, —$SO_2NR_5R_6$, —$SO_2R_5$, —$CH_2$—OH, halogen, phthalimidyl, thiophenyl, pyrrolyl, pyrrolinyl, and oxazolyl, or, alternatively, $R_1$ and $R_2$ together with two or more of the phenyl carbon atoms form a —$O(CH_2)_mO$— ring, wherein m is 1 or 2;

$R_3$ and $R_4$ are joined together to form a heterocylic ring containing 4 to 8 carbon atoms with the nitrogen atom to which they are attached; and Each of $R_5$ and $R_6$ is independently selected from the group consisting of H, $(C_1$-$C_8)$ alkyl, $(C_2$-$C_8)$ alkenyl, and $(C_3$-$C_8)$ cycloalkyl.

According to some of any of the embodiments of the present invention, at least one of $R_3$ and $R_4$ is H.

According to some of any of the embodiments of the present invention, $R_3$ or $R_4$ is propyl.

According to some of any of the embodiments of the present invention, each of $R_1$ and $R_2$ is independently H, —$OCH_3$, or —$OSO_2CF_3$, or $R_1$ and $R_2$ together with two or more of the phenyl carbon atom form a —$O(CH_2)_mO$— ring, wherein m is 1 or 2.

According to some of any of the embodiments of the present invention, the compound of Formula I is selected from: 5-methoxy-2-aminoindan; and 5,6-dimethoxy-2-aminoindan.

According to some of any of the embodiments of the present invention, the compound forms a part of a composition which further comprises a pharmaceutically acceptable carrier.

According to some of any of the embodiments of the present invention, the compound or composition are formulated for oral administration.

According to some of any of the embodiments of the present invention, the composition is in a form of a free-flowing powder, a tablet, a capsule, a lozenge, a liquid, a liquid concentrate or a syrup.

According to some of any of the embodiments of the present invention, the composition is a unit dosage form composition.

According to some of any of the embodiments of the present invention, an amount of the compound in the unit dosage form ranges from 30 mg to 130 mg.

According to some of any of the embodiments of the present invention, the amount of the compound is 70 mg.

According to some of any of the embodiments of the present invention, the compound or composition is administered to a subject orally.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to binge behavior, and more particularly, but not exclusively, to compositions and methods for regulation of binge behavior, such binge drinking.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

A discussed hereinabove, different binge behaviors have similar causes, whether it's drinking, eating, smoking, shopping, or sexual conduct, and that all types of bingeing are ways of dealing with negative emotions that are not rational or healthy.

The terms "binge", "binge behavior", "binge disorder", "bingeing" and "bingeing behavior" as used herein are interchangeable and relate to non-controlled excessive behavior of indulgence in a variety of activities such as eating, drinking, smoking, drugs use, shopping, sexual conduct, and the like. Binge behavior includes intensive, short episodes of overuse and over consumption of food, alcohol, smoking products, drugs, sweets, sex and the like. Bingeing behaviors are compulsive in style, intensity, habituation, history, motivation, and difficulty to control and remediate. "Compulsive behavior", as used herein refers to driven behaviors which are often influenced by subconscious desires and motives, as well as strong, uncontrollable, hard-to-tame actions and behaviors which have a predictable pattern.

The present inventor has uncovered that when certain psychoactive compounds that up-regulate the dopamine receptors D2 and D3 in the CNS are consumed together with alcoholic beverages, for example, an amount of 70 mg of powder form of an antipsychotic that regulates DA occupancy at dopamine receptors, dissolved in at least one whiskey shot or in at least one beer glass during a night of drinking, the added compound imparts a feeling of satisfaction, satiety or contentedness which halt or discourage the drinker from consuming more alcohol, thereby discouraging binge drinking behavior.

Mixing these compounds in certain amounts of liquid does not impair the inebriating feeling of consuming beer or wine or a spirit in their user's experience. However, consuming these compounds imparts to the consumer a feeling of satisfaction, satiety or contentedness which discourages binge behavior. These compounds, although intoxicating in a way similar to alcohol (at least at low dosages) and even having some anxiolytic and sedative effects, are not harmful in terms of motor, cognitive and addictive effects attributed to consumption of alcoholic beverages.

Embodiments of the present invention therefore relate to a method for binge mitigation utilizing certain aminoindan derivatives known as DRD2 and/or DRD3 regulators, which provide the person engaged in a binging behavior such as binge drinking, binge eating, binge smoking and the like, psychotropic effects such as a feeling of satisfaction, satiety or contentedness which discourages, moderate or halt the binging.

Embodiments of the present invention concern controlling, or regulating, binge behavior, such as, but not limited to, binge drinking, while utilizing aminoindan derivatives, more particularly 2-aminoindan derivatives, collectively represented by Formula I as presented herein.

Exemplary embodiments of the present invention are of alcoholic beverages such as 300 ml beer or wine or 100 ml whiskey which are mixed with 30-130 mg of a 2-aminoindan derivative and consumed during a drinking session.

According to an aspect of some embodiments of the present invention, there is provided a method of regulating binge behavior in a subject in need thereof, which is effected by administering to the subject an aminoindan derivative, more particularly, a 2-aminoindan derivative, represented by Formula I as described herein.

A 2-aminoindan derivative as described herein is referred to herein mainly as a "binge regulating agent", "binge mitigating agent" or "binge regulator", but also as "drinking regulator", "drinking restrictor", "drinking-control agent", "anti-bingeing agent" or "self-control drug".

In the context of the present embodiments, regulating binge behavior is also referred to herein interchangeably as controlling or mitigating binge behavior, or as treating a binge disorder, and concerns controlling the excessive, compulsive behavior of indulgence, by, for example, reducing the uncontrollable need of a binged person to consume food, alcohol, sex, tobacco, sweets or to shop, or any other subject of excessive compulsive consumption (binge's subject). Regulating binge behavior therefore relates to restraining or moderating the compulsive behavior as defined herein, namely, restraining or moderating the strong, uncontrollable, hard-to-tame actions and behaviors which have a predictable pattern. In some embodiments, regulating binge behavior is considered as treating a binge disorder, as described herein.

In some of any of the embodiments described herein, regulating binge behavior describes reducing a consumption of the binge's subject (e.g., alcoholic drink, food, smoking or tobacco product, drug, sweets, sexual conduct, shopping) during a binge episode and/or in reducing the occurrence of episodes of binge behavior during a certain time period. In some of these embodiments, consumption is reduced by at least 10%, or at least 20%, or at least 30, or at least 40%, or at least 50%, and even by 60%, 70% or more, compared to episodes without administering the binge regulating agent described herein. Alternatively, or in addition, the number of episodes of binge behavior during a certain time period (e.g., a week or a month or a year) is reduced by at least 10%, or at least 20%, or at least 30%, or at least 40%, or at least 50%, and even by 60%, 70% or more.

Controlling a binge behavior may result in substantially reducing the harmful effects associated with, and/or harmful consequences of, a binge behavior.

Regulating binge behavior as described herein can therefore be used for harm reduction.

"Harm reduction", in a broad interpretation refers to any intervention that reduces the harmful effects of bingeing, as defined herein. Harm reduction includes social measures as well as medications to ameliorate, reduce, moderate or prevent harmful effects and consequences associated with a compulsive binge behavior, such as harmful mental, psychological, physiological, economical, social and cultural effects exhibited by a subject engaged in a binge behavior. Harm reduction is obtainable, for example, by regulating binge behavior.

A subject in need of regulating a binge behavior is typically a subject that experiences episodes of over consumption of the binge's subject (e.g., food, alcohol, smoking, drug use, sweets, sex, shopping, etc.), either on a regular basis, for example, more than once a week, or occasionally, or even rarely, for example once or twice a year, depending on the severity of the binges. Blackout drinkers, for example, that experience a blackout when consuming alcohol even as rarely as twice per year are defined herein as subjects is need of regulating binge drinking. Determining a subject in need of regulating binge behavior can be made, in some cases, according to national or international standards, or by acceptable evaluations by health professionals (e.g., physicians, psychologists, cognitive therapists, social workers, nutritionists, etc., depending on the binge disorder).

In some of any of the embodiments of the present invention, binge behavior is associated with alcohol consumption, tobacco consumption, eating, shopping and/or sexual conduct.

In some of any of the embodiments of the present invention, the binge regulator represented by Formula I as described herein is utilized (e.g., administered, or self-administered), either before, simultaneously with, or subsequent to consumption of a binge's subject. For example, it is utilized before, during or subsequent to a meal or other eating event, a drinking session or other drinking event, a shopping episode, and/or in accordance with a subject's habitudes, for example, in accordance with times or events of binge smoking, binge sex, binge shopping, etc.

An effective amount of binge mitigating agent is an amount that when administered to the subject regulates binge behavior, as described herein.

The effective amount depends inter alia on the type of binge behavior, its severity, its occurrence, and on several other factors, and can be determined by a health professional and/or by the subject himself.

In exemplary embodiments, the effective amount that is administered to a subject to regulate a single episode of binge behavior is in a range of from 30 mg to 800 mg.

The effective amount can be administered to the subject at once, in a single dose, or be divided to several doses over the time of bingeing or can be administered per day over a period of time, per a desired regimen as follows.

Depending on the type and severity of the binge disorder, the binge mitigation agent can be administered in a chronic regimen (namely, every day, every other day, twice a week, once a week, or twice or more a day), or "per demand", namely, before, during or subsequent a binge behavior, as described herein.

Administering the binge regulating agent can be made according to a dosage and/or regimen recommended by a health professional or can be self-administering by the subject per the subject's demands (for example, when a subject determines he is in need of regulating a binge behavior).

According to some of any of the embodiments described herein, the method of regulating binge behavior is for regulating binge drinking.

In the context of embodiments of the present invention, regulating binge drinking relates to controlling the excessive behavior of indulgence in drinking alcoholic beverages. For example, regulating binge drinking may involve reducing the amount of alcohol consumed in a drinking session and/or the number of drinking sessions in a week, per the embodiments described hereinabove.

Regulating binge drinking provides restraining or moderating the compulsive uncontrollable, behavior associated with binge drinking thereby reducing the harmful consequences associated with excessive alcohol consumption, while not impairing the psychological and social pleasures associated with the drinking.

The phrase "binge drinking" or "binge drinking disorder" as used herein is determined according national or international definitions as defined by regulation authorities, for example, in line with the definition of binge drinking used by the National Health Service (NHS) and the National Office of Statistics in the United Kingdom (UK), and corresponding services, offices and/or authorities in other countries. The definition of binge drinking used by NHS and the National Office of Statistics describes it as drinking more than double the lower risk guidelines for alcohol in one drinking session, wherein the guidelines advise that people should not regularly drink more than the lower risk guidelines of 3-4 units of alcohol for men (equivalent to a pint and a half of 4% beer (about 852 ml)) and 2-3 units of alcohol for women (equivalent to a 175 ml glass of wine). "Regularly" means drinking every day or most days of the week.

"One unit of alcohol" as defined herein and acceptable in the art is 10 ml of pure alcohol. It takes an average adult around an hour to process this so that there's none left in the bloodstream, although this varies from person to person.

In some embodiments, binge drinking for men, therefore, is regularly drinking more than 8 units of alcohol—or about three pints of strong beer. For women, it's regularly drinking more than 6 units of alcohol, equivalent to 2¼ pints of strong beer or two large glasses of wine.

In an aspect of some embodiments of the present invention, there is provided a method of regulating consumption of an alcoholic beverage in a subject in need thereof, the method being effected by administering to the subject a compound represented by Formula I as described herein. In some embodiments, the consumption of alcohol beverages is excessive and uncontrolled as in binge drinking. In some embodiments, the subject is determined as having a binge drinking disorder, as defined herein. In some of these embodiments, the method provided herein is for regulating binge drinking or treating a binge drinking disorder in a subject in need thereof.

In some embodiments, the method provided herein is for reducing alcohol consumption in a non-binger subject who wishes to control his alcohol consumption, for example, under certain circumstances (for example, during a specific event or time point).

The term "binge drinking regulation" in a broad interpretation refers to controlling the excessive, uncontrolled consumption of alcoholic beverages. Regulating binge drinking relates to reducing the amount of alcohol consumed in a drinking session and/or reducing the number of drinking sessions.

In the context of embodiments of the present invention, binge drinking regulation relates to imparting a feeling of satisfaction, satiety or contentedness which discourages binge drinking. Binge drinking regulation as practiced in embodiments of the present invention effects a true harm reduction utility by discouraging binge drinking in a way that is easy to implement (by drinking) and non harmful (pending toxicological validation) to the drinker.

In some of any of the embodiments of the present invention, the binge regulator represented by Formula I as described herein is administered either before, simultaneously with, or subsequent to consumption of an alcoholic beverage.

An effective amount of a binge regulating agent in the context of these embodiments of the present invention is an amount that when consumed either before, simultaneously with or subsequently after consumption of an alcoholic beverage, will regulate (e.g., discourage) binge drinking.

The overall amount of the binge regulating agent that when administered before, simultaneously with or subsequently following, a binge drinking episode, and is effective in discouraging immediate (soon to happen), ongoing or continued binge drinking, depends on the mental and physical situation of the subject in need of binge drinking mitigation. In some embodiments, the effective amount, namely the total amount that would prevent, moderate, halt or discourage binge drinking in a single episode of binge drinking (e.g., in a single drinking session) is in a range of from 30 mg to 400 mg, and sometimes even up to 800 mg.

As discussed in further detail herein, the effective amount can be administered to the subject at once, in a single dose, or be divided to several doses administered during a binge drinking episode (e.g., a drinking session).

According to some embodiments of the this aspect of the present invention, unit dosage forms of a binge regulating agent as represented by Formula I as described herein are utilized, whereby each unit dosage form comprises one or more derivatives of a 2-aminoindan of Formula I as described herein in an amount within a range of from 30 mg to 130 mg, from 30 mg to 120 mg, from 40 mg to 120 mg, from 40 mg to 110 mg, from 50 mg to 110 mg, from 50 mg to 100 mg, from 50 mg to 90 mg, from 60 mg to 90 mg, or from 60 mg to 80 mg, and any intermediates therebetween.

In exemplary embodiments, a unit dosage form contains 70 mg or 80 mg of a binge regulating agent as described herein.

In exemplary embodiments, 1-10 such unit dosage forms are administered to the subject during a single drinking session.

In exemplary embodiments, administration of the amount of 70 mg of drinking regulator selected form Compound 1 or Compound 2 described herein reduced the amount of beer drunk in a binge session from 1.5 liter to 0.5 liter, or the amount of wine drunk in a binge session from 1000 ml to 250 ml.

In some embodiments, the binge regulating agent represented by Formula I and the alcoholic beverage are consumed simultaneously, for example, by introducing (e.g., dissolving or mixing) the binge regulating agent with the alcoholic beverage.

In embodiments wherein the binge regulating agent is being mixed with a beverage, for example an alcoholic beverage, the amount of said binge regulating agent is in a range selected from 0.15 mg/ml to 0.60 mg/ml, 0.15 mg/ml to 0.50 mg/ml, 0.15 to 0.40 mg/ml, 0.18 to 0.50 mg/ml, 0.18 to 0.40 mg/ml, 0.20 to 0.40 mg/ml, 0.20 to 0.30 mg/ml, 0.20 to 0.25 mg/ml, or 0.20 to 0.23 mg/ml.

In some embodiments, the drinker himself mixes or dissolves the drinking regulating agent with the alcoholic drink, such that the binge regulating agent is self-administered. In some other embodiments, the alcoholic beverage provided to the drinker already contains the binge regulating agent.

In some embodiments, the binge regulating agent is taken-up first, before the alcoholic beverage is consumed. In the context of these embodiments, the binge regulating agent is taken by the drinker (self-administered) about 15 minutes, about 20 minutes, about 30 minutes, about 40 minutes, about 50 minutes, 60 minutes, 70 minutes, 80 minutes, 90 minutes 120 minutes, 150 minutes, or about 180 minutes, before alcohol is consumed and any intermediate times there between.

In some embodiments, the binge regulating agent is taken-up subsequently following alcohol consumption. In the context of these embodiments, the binge regulating agent is taken by the drinker (self-administered) about 5 minutes, about 7 minutes, about 10 minutes, about 15 minutes, about 20 minutes, about 25 minutes, 30 minutes, about 35 minutes, about 40 minutes or about 45 minutes, after the first or second or third or fourth drink, and any intermediate times there between. Preferably, the binge regulating agent is consumed (e.g., self-administered) following the first or second drink.

Administration of an effective amount of the binge regulating agent as described herein, whether alone or in combination with an alcoholic beverage, to a subject will detectably reduce the amount of alcohol consumed in a binge drinking, and will prevent many of the adverse affects associated with excessive alcohol consumption particularly short-term effects such as heavy intoxication that leads to serious consequences such as accidents and uncontrolled violent behavior with subsequent medical complications, as well as gastric irritation, anxiety disorders and other excitable states.

In some embodiments, administering the binge regulating agent to a subject (e.g., self-administering) yields a reduction in alcohol consumption by at least about 10%, 20%, 30%, 50%, 60% or greater, up to about 75-90%, or about 95% or greater. In some embodiments, this reduction in alcohol consumption is during a single drinking session when the binge regulating agent is administered. In some embodiments, this reduction is during a period of time (e.g., a week), and may result from administering the agent during every drinking session, or by reducing the occurrences of drinking sessions as a result of a single or multiple administrations of the agent.

The effectiveness of mitigation of binge drinking can be measured in several ways. For example, subjects can self-report according to guidelines and procedures set up for such reporting. Objective measures of alcohol consumption include the use of breath alcohol-meter readings, measuring serum CDT levels, and measuring serum γ-glutamyl transferase (GGT) levels. Urinary 5-HTOL may also be measured and is an indicator of recent alcohol consumption. 5-HTOL is a minor metabolite of 5-HT. Other subjective and objective measures are also known. These measurements can be taken or performed at various times before, during, and after consumbution of the binge regulator.

The term "alcoholic beverage" as used herein encompasses any beverage having an alcoholic content of at least 2% by volume, whether distilled, fortified, brewed, or produced by fermentation, and includes, but is not limited to, wine, beer, fermented liquids derived in whole or in part from fruit juices, such as cider and perry, spirits, flavored alcoholic beverages collectively termed herein and in the art as "alcopops", and the like.

In some embodiments, the alcoholic beverage is an authentic beverage, for example, beer, wine, or any kind of spirit, that contains the original amount of alcohol, for example, 5% by volume in beer, 13% in wine and 30% in a spirit. The term "wine" as used herein and in the art includes the fermented juice of grapes, made in many varieties, such as red, white, sweet, dry, still, and sparkling. Exemplary wine beverages include, but are not limited to, dry red or white wine, semi-dray red or white wine, rose wine, dessert wine, Port wine, Champagne, sparkling wine, and vermouth. Typical alcoholic wine beverages include an alcoholic content of 10-14%.

Herein throughout, whenever a percentage (%) is indicated, volume % of the total volume of the beverage is meant, unless otherwise indicated.

The term "beer" as used herein and in the art means beverages obtained by malting and fermenting some one or more of the cereal grains, and includes ale, stout, porter and lager.

The term "spirit" as used herein and in the art refers to distilled alcohol beverages obtained, for example, by distilling starchy material and include, but not limited to, variety of raw grain alcohols, brandies, liquors, saki, Ouzo, arrack, rum, vodka, tequila, schnapps, whiskey, gin, cordial, Cachaça, absinthe, baijiu, eau de vie, soju, aguardiente, palinka, fernet and slivovitz.

The binge regulating agent described herein can be administered together with additional therapeutic agents administered as combination therapies to treat alcohol-related disorders. The additional therapeutic agents include, but are not limited to, traditional anti-alcohol agents and/or other agents as described herein above and known in the art, such as disulfiram; naltrexone; acamprosate (Campral®); ondansetron; sertraline (Zoloft®); tiapride; gamma hydroxybutyrate (Alcover®); galantamine; nalmefene (Revex); naloxone; benzodiazepines; neuroleptics such as laevomepromazine (Neurocil®) and thioridazine (Melleril®); piracetam; clonidine; carbamazepine; clomethiazole (Distraneurin®); levetiracetam; quetiapine; risperidone; rimonabant; trazodone; topiramate; aripiprazole; amperozide; and modafinil.

The binge regulating agent as described herein for any one of the methods described herein and any embodiments thereof can also be administered to a subject in combination with behavioral therapy or interaction.

In some embodiments, binge mitigation is further supplemented by providing to subjects a form of psychosocial intervention and/or management, such as Brief Behavioral Compliance Enhancement Treatment (BBCET). BBCET, a standardized, manual-guided, brief (i.e., delivered in about 15 minutes), psychosocial adherence enhancement procedure, emphasizes that medication/binge mitigation compliance is crucial to changing participants' drinking behavior (Johnson et al., Brief Behavioral Compliance Enhancement Treatment (BBCET) manual. In: Johnson B A, Ruiz P, Galanter M, eds. Handbook of clinical alcoholism treatment. Baltimore, Md.: Lippincott Williams & Wilkins; 2003, 282-301). Brief interventions such as BBCET, have been shown to benefit treatment of alcohol dependence. Psychosocial management regimens other than BBCET may also be used, including, but not limited to, Cognitive Behavioral Coping Skills Therapy (CBT) (Project MATCH Research Group. Matching Alcoholism Treatments to Client Heterogeneity: Project MATCH posttreatment drinking outcomes. J Stud Alcohol. 1997; 58:7-29), Motivational Enhancement Therapy (MET) (Project MATCH Research Group. Matching Alcoholism Treatments to Client Heterogeneity: Project MATCH posttreatment drinking outcomes. J. Stud. Alcohol. 1997, 58:7-29), Twelve-Step Facilitation Therapy (TSF) (Project MATCH Research Group. Matching Alcoholism Treatments to Client Heterogeneity: Project MATCH posttreatment drinking outcomes. J. Stud. Alcohol. 1997, 58:7-29), Combined Behavioral Intervention (CBI), (Anton et al., JAMA, 2006, 295:2003-2017) Medical Management (MM) (Anton et al., JAMA, 2006, 295:2003-2017), or the Biopsychosocial, Report, Empathy, Needs, Direct advice, and Assessment (BRENDA) model (Garbutt et al., JAMA, 2005, 293:1617-1625). Alternative interventions such as hypnosis or acupuncture may also be employed together with binge mitigation described herein in order to assist in treating an addictive alcohol use.

Any one of the methods and uses described herein, including any embodiments and combination thereof, utilize a compound represented by Formula I:

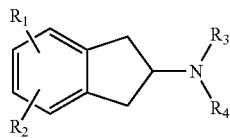

Formula I wherein:

each of $R_1$ and $R_2$ is independently selected from the group consisting of H, $(C_1-C_8)$alkyl, $(C_2-C_4)$alkenyl, $(C_2-C_8)$alkynyl, $(C_3-C_8)$cycloalkyl, aryl, heteroaryl, heteroalicyclic, —O$(C_1-C_6)$alkyl, OH, —OS(=O)$_2$CF$_3$, —OS(=O)$_2$—$(C_1-C_6)$alkyl, —S(=O)R$_5$, —CO$_2$R$_5$, —CONH$_2$, —CONR$_5$R$_6$, —COR$_5$, —CF$_3$, CN, —SRS, —SO$_2$NH$_2$, —SO$_2$NR$_5$R$_6$, —SO$_2$R$_5$, —OCO—$(C_1-C_6)$alkyl, —NCO—$(C_1-C_6)$alkyl, —CH$_2$O—$(C_1-C_6)$alkyl, —$(C_1-C_6)$alkyl-OH, —CO-aryl, —NHSO$_2$-aryl, —NHSO$_2$—$(C_1-C_{15})$alkyl, and halogen, or, alternatively, $R_1$ and $R_2$ together with two or more of the phenyl carbon atoms form a —X$_1$—(CR$_5$R$_6$)$_m$—X$_2$— ring, wherein each of X$_1$ and X$_2$ is independently selected from C, O, NH or S and m is 1, 2, 3, or 4;

each of $R_3$ and $R_4$ is independently selected from the group consisting of H, $(C_1-C_8)$alkyl, $(C_2-C_8)$alkenyl, $(C_2-C_8)$alkynyl, $(C_3-C_8)$ cycloalkyl, and —(CH$_2$)$_p$-thienyl, wherein p is 1, 2, 3, or 4, or alternatively, $R_3$ and $R_4$ are joined together to form a heterocylic ring (heteroalicyclic or heteroaryl) containing the nitrogen atom to which they are attached; and each of $R_5$ and $R_6$ is independently selected from the group consisting of H, $(C_1-C_8)$alkyl, $(C_2-C_8)$alkenyl, $(C_3-C_8)$cycloalkyl and aryl.

In some embodiments of the invention, the 2-aminoindan derivative of the Formula I is as presented herein, wherein $R_1$-$R_6$ are defined as follows:

each of $R_1$ and $R_2$ is independently selected from the group consisting of H, $(C_1-C_8)$alkyl, $(C_2-C_8)$alkenyl, $(C_2-C_8)$alkynyl, $(C_3-C_8)$cycloalkyl, aryl, —OCH$_3$, OH, —OSO$_2$CF$_3$, —OSO$_2$CH$_3$, —SORB, —CO$_2$R$_5$, —CONR$_5$R$_6$, —COR$_5$, —CF$_3$, —CN, —SRS, —SO$_2$NR$_5$R$_6$, —SO$_2$R$_5$, —CH$_2$—OH, halogen, phthalimidyl, thiophenyl, pyrrolyl, pyrrolinyl, and oxazolyl, or, alternatively, $R_1$ and $R_2$ together with two or more of the phenyl carbon atoms form a —O(CH$_2$)$_m$O— ring, wherein m is 1 or 2;

$R_3$ and $R_4$ are joined together to form a heterocylic ring containing 4 to 8 carbon atoms with the nitrogen atom to which they are attached; and each of $R_5$ and $R_6$ is independently selected from the group consisting of H, $(C_1-C_8)$ alkyl, $(C_2-C_8)$ alkenyl, and $(C_3-C_8)$ cycloalkyl.

In some embodiments, the compound of Formula I is as described herein wherein the amino group is a secondary or tertiary amine, namely at least one of $R_3$ and $R_4$ is an alkyl, for example, propyl. Secondary (or tertiary) amino groups are preferred as the 2-aminoindan derivatives containing a secondary (or tertiary) amine moiety are less susceptible to enzymatic degradation by e.g., monoamine oxidase (MAO) enzymes and are thus more potent than primary amines when acting in the brain. In addition, secondary or tertiary amines are more hydrophobic and hence are more brain permeable.

In some embodiments, the compound of the Formula I is as described herein, wherein $R_1$ and $R_2$ each independently is H, —OCH$_3$, or —OSO$_2$CF$_3$, or $R_1$ and $R_2$ together with two or more of the phenyl carbon atom form a —O(CH$_2$)$_m$O— ring, wherein m is 1 or 2.

Non-limiting examples of 2-aminoindan derivatives, which may be used in the context of the present embodiments, include:

(1) 5-methoxy-2-aminoindan;
(2) 5,6-dimethoxy-2-aminoindan;
(3) 5-methoxy-2-(N-propylamino)indan;
(4) 5,6-dimethoxy-2-(N-propylamino)indan;
(5) 5,6-dimethoxy-2-(di-N-butylamino)indan;
(6) 5-(trifluoromethylsulfonyloxy)-6-hydroxy-2-(di-N-propylamino)indan;
(7) 5-(trifluoromethylsulfonyloxy)-2-(N-propylamino)indan;
(8) 5,6-(di-trifluoromethylsulfonyloxy)-2-(N-propylamino) Indan;
(9) 5,6-dimethoxy-2(pyrrolidino)indan;
(10) 5-(trifluoromethylsulfonyloxy)-6-acetoxy-2-(di-N-propylamino)indan;
(11) 5-trifluromethansulfonyloxy-6-methoxy-2-(di-N-propylamino)indan;
(12) 5,6-ethylenedioxy-2-(di-N-propylamino)indan;
(13) 5,6-methylenedioxy-2-(di-N-propylamino)indan;
(14) 5-hydroxy-2-(n-propylamino)indan;

(15) 5,6-dihydroxy-2-(n-propylamino)indan;
(16) 4-methyl-2-aminoindan;
(17) 4,5-di-methyl-2-aminoindan;
(18) 5,6-di-methyl-2-aminoindan;
(19) 6-methyl-2-aminoindan;
(20) 4-fluoro-2-aminoindan;
(21) 5-(i-propyl)-2-aminoindan;
(22) 4,6-dimethyl-2-aminoindan;
(23) 4,7-dimethyl-2-aminoindan;
(24) 5-(t-butyl)-2-aminoindan;
(25) 5-propyl-2-aminoindan;
(26) 5-fluoro-2-(di-N-propylamino)indan;
(27) 6-methylenedioxy-2-(di-N-propylamino)indan;
(28) 5,6-dimethoxy-2(pyrrolidino)indan;
(29) 5,6-(di-carbomethoxy)-2-(di-N-propylamino)indan;
(30) 5-(carbomethoxy)-6-hydroxy-2-(di-N-propylamino)indan;
(31) 5-bromo-2-(dipropylamino)indan;
(32) (6-methylsulfanyl-indan-2-yl)-dipropyl-amine;
(33) (6-methylsulfonyl-indan-2-yl)-dipropyl-amine;
(34) (6-methylsulfinyl-indan-2-yl)-dipropyl-amine;
(35) 2-dipropylamino-indan-5-carbaldehyde;
(36) (5-iodo-indan-2-yl)-dipropyl-amine;
(37) (4-iodo-indan-2-yl)-dipropyl-amine;
(38) toluene-4-sulfonic acid 2-dipropylamino-indan-5-yl ester;
(39) toluene-4-sulfonic acid 2-dipropylamino-6-hydroxy-indan-5-yl ester;
(40) N-[2-(benzyl-propylamino)-indan-5-yl]-4-methyl benzene-sulfonamide;
(41) N-[2-(benzyl-propyl-amino)-indan-5-yl]methanesulfonamide;
(42) 2-[2-(benzyl-propyl-amino)-indan-5-yl]-isoindole-1,3-dione;
(43) benzyl-propyl-(6-pyrrol-1-yl-indan-2-yl)-amine;
(44) propyl-(6-pyrrol-1-yl-indan-2-yl)-amine;
(45) propyl-(6-pyrrolidin-1-yl-indan-2-yl)-amine;
(46) dipropyl-(6-pyrrolidin-1-yl-indan-2-yl)-amine;
(47) cyclopropanecarboxylic acid-[2-(benzyl-propyl-amino)-indan-5-yl]acetamide;
(48) N-[2-(benzyl-propyl-amino)-indan-5-yl]propionamide;
(49) N-[2-(benzyl-propyl-amino)-indan-5-yl]-2,2-dimethyl propionamide;
(50) 5-(2-propenyloxy)-2-(di-N-propylamino)-indan;
(51) 5,6 di-toluenesulfonyloxy-2-(di-N-propylamino)indan;
(52) 5-methanesulfonyloxy-2-(di-N-propylamino)indan;
(53) 5-carbomethoxy-2-(di-N-propylamino)indan;
(54) 5-carboxamido-2-(di-N-propylamino)indan;
(55) 5,6-di-triluuomethansulfonyloxy-2-(propylamino)indan;
(56) 4-methyl-2-(di-N-propylamino)indan;
(57) 4,5-di-methyl-2-(di-N-propylamino)indan;
(58) 5,6-di-methyl-2-(di-N-propylamino)indan;
(59) 5-methyl-2-(di-N-propylamino)indan;
(60) 4-fluoro-2-(N-propyl)aminoindan;
(61) 5-(i-propyl)-2-(di-N-propylamino)indan;
(62) 5-(i-propyl)-2-(N-propylamino)indan;
(63) 4,6-dimethyl-2-(di-N-propylamino)indan;
(64) 4,7-dimethyl-2-(di-N-propylamino)indan;
(65) 5-propyl-2-(di-N-propylamino)indan;
(66) 5-(t-butyl)-2-(dim-propylamino)indan;
(67) 5-trifluoromethyl-2-(di-N-propylamino)indan;
(68) 5-sulfoxamido-2-(di-N-propylamino)indan;
(69) 5-(3-thiophene)-2-(di-N-propylamino)indan;
(70) 5-ethynyl-2-(di-N-propylamino)indan;
(71) 5-acetyl-2-(di-N-propylamino)indan;
(72) 5-cyano-2-(di-N-propylamino)indan;
(73) 5-carbomethoxy-6-acetoxy-2-(di-N-propylamino)indan;
(74) 5-carbomethoxy-6-trifluoromethanesulfonyloxy-2-(di-N-propylamino) indan;
(75) 5-carbomethoxy-6-methoxy-2-(di-N-propylamino)indan;
(76) 5-formyl-6-methoxy-2-(di-N-propylamino)indan;
(77) 5-hydroxymethyl-6-methoxy-2-(di-N-propylamino)indan;
(78) 5-carboxy-6-methoxy-2-(di-N-propylamino)indan;
(79) 5-acetyl-6-methoxy-2-(di-N-propylamino)indan;
(80) 5-carboxamido-6-methoxy-2-(di-N-propylamino)indan;
(81) 5-ethynyl-6-methoxy-2-(di-N-propylamino)indan;
(82) 5-cyano-6-methoxy-2-(di-N-propylamino)indan; and
(83) 5,6-di-(hydroxymethyl-2-(di-N-propylamino)indan.

In some of any of the embodiments described herein, the 2-aminoindan derivative of Formula I is any one of the compounds (1)-(13) above, in which the phenyl moiety is substituted by one or two —OCH$_3$, or —OSO$_2$CF$_3$ groups, or the phenyl moiety bears a —O(CH$_2$)$_m$O— ring, wherein m is 1 or 2, fused thereto. The structural formulas of compounds 1-13 are depicted in Table A hereinunder.

In exemplary embodiments, the 2-aminoindan derivative used is 5-methoxy-2-aminoindan (Compound 1) or 5,6-dimethoxy-2-aminoindan (Compound 2), the chemical structures of which are depicted hereinbelow.

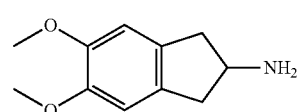

Compound 1

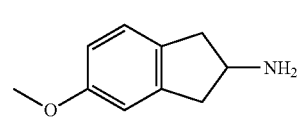

Compound 2

TABLE A

| Compound No. | Name | Structure |
| --- | --- | --- |
| 1 | 5-methoxy-2-aminoindan | 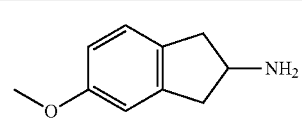 |

TABLE A-continued
| Compound No. | Name | Structure |
|---|---|---|
| 2 | 5,6-dimethoxy-2-aminoindan | 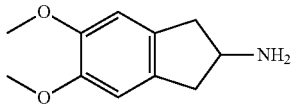 |
| 3 | 5-methoxy-2-(N-propylamino)indan | 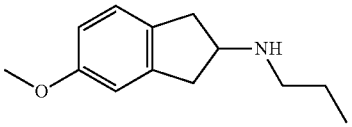 |
| 4 | 5,6-dimethoxy-2-(N-propylamino)indan | 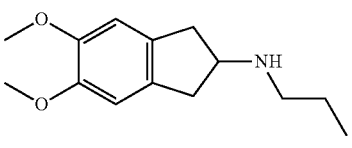 [SMILES: CCCNC1Cc2cc(OC)c(OC)cc2C1] |
| 5 | 5,6-dimethoxy-2-(di-N-butylamino)indan | 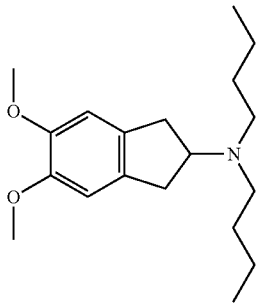 [SMILES: CCCCN(CCCC)C1Cc2cc(OC)c(OC)cc2C1] |
| 6 | 5-(trifluoromethyl-sulfonyloxy)-6-hydroxy-2-(di-N-propylamino)indan | 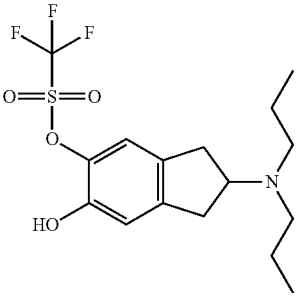 [SMILES: CCCN(CCC)C1Cc2cc(O)c(OS(=O)(=O)C(F)(F)F)cc2C1] |
| 7 | 5-(trifluoromethyl-sulfonyloxy)-2-(N-propylamino)indan | 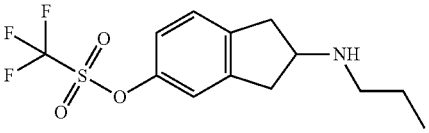 [SMILES: CCCNC1Cc2ccc(OS(=O)(=O)C(F)(F)F)cc2C1] |
| 8 | 5,6-(di-trifluoromethyl-sulfonyloxy)-2-(N-propylamino)indan | 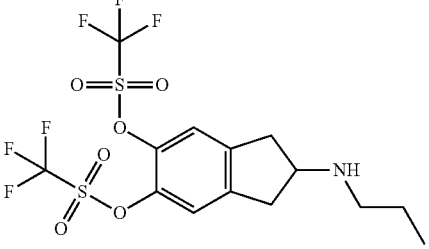 |
| 9 | 5,6-dimethoxy-2-(pyrrolidino)indan | 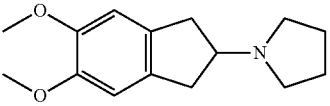 [SMILES: COc1cc2c(cc1OC)CC(N1CCCC1)C2] |

TABLE A-continued

| Compound No. | Name | Structure |
|---|---|---|
| 10 | 5-(trifluoro-methylsulfonyloxy)-6-acetoxy-2-(di-N-propylamino)indan | 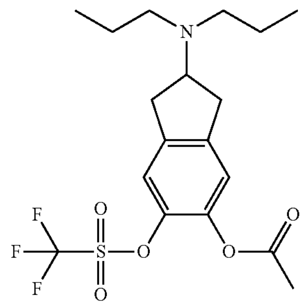 [SMILES: CCCN(CCC)C1Cc2cc(OC(C)=O)c(OS(=O)(=O)C(F)(F)F)cc2C1] |
| 11 | 5-trifluoro-methansulfonyloxy-6-methoxy-2-(di-N-propylamino)indan | 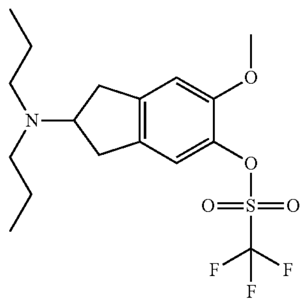 [SMILES: CCCN(CCC)C1Cc2cc(OC)c(OS(=O)(=O)C(F)(F)F)cc2C1] |
| 12 | 5,6-ethylenedioxy-2-(di-N-propylamino)indan | 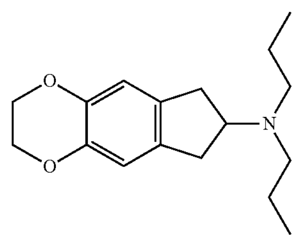 [SMILES: CCCN(CCC)C1Cc2cc3c(cc2C1)OCCO3] |
| 13 | 5,6-methylenedioxy-2-(di-N-propylamino)indan | 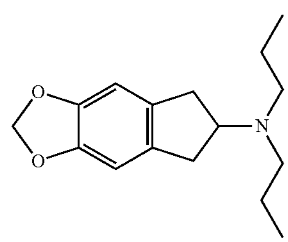 [SMILES: CCCN(CCC)C1Cc2cc3c(cc2C1)OCO3] |

In any one of the embodiments described herein, each of the compounds described herein can further be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more basic groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

In the context of some of the present embodiments, a pharmaceutically acceptable salt of the compounds described herein may optionally be a base addition salt comprising at least one group of the compound which is in a form of an anion, in combination with at least one counter ion (i.e., cation) that forms a pharmaceutically acceptable salt. Examples of suitable cations include metal cations of metals such as, but not limited to, sodium, potassium, magnesium, and calcium or ammonium.

Each of these base addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

Further, in any one of the embodiments described herein, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the 2-aminoindan derivatives described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

The compounds represented by Formula I as described herein may be prepared according to methods and practices known in the art, for example, as taught in U.S. Pat. No. 5,708,018, which is incorporated by reference as if fully set forth herein.

According to an aspect of some embodiments of the present invention, there is provided a compound represented by Formula I as described herein, in any one of the respective embodiments, and any combination thereof, for use in regulating a binge behavior, as defined herein, or in the manufacture of a medicament for regulating a binge behavior as described herein.

According to an aspect of some embodiments of the present invention, there is provided a compound represented by Formula I as described herein, in any one of the respective embodiments, and any combination thereof, for use in reducing a consumption of an alcoholic beverage, as defined herein, or in the manufacture of a medicament for reducing a consumption of an alcoholic beverage, as described herein.

In any one of the methods and uses described herein, including any one of embodiments thereof, the compound of Formula I described herein may form a part of a composition, which further comprises a pharmaceutically acceptable carrier, and in some embodiments, the composition is for use in a method of regulating binge behavior, for example binge drinking, or regulating alcohol consumption for example excessive alcohol consumption, as defined herein.

Pharmaceutical compositions comprising the compound of Formula I as described herein, may be administered systemically in oral solid or oral liquid formulations, or as suppository, aerosol, topical or other similar formulations. In preferred embodiments, the binge regulator or a composition comprising same is administered to a subject orally.

An aspect of some embodiments of the present invention relates to the preparation of pharmaceutical compositions comprising a derivative of 2-aminoindan useful for regulating a binge behavior as described herein.

In addition to a derivative of 2-aminoindan as an active ingredient, such pharmaceutical compositions may contain one or more pharmaceutically-acceptable carriers and other ingredients known to enhance and facilitate drug administration.

The active ingredient may be present in the pharmaceutical composition in the form of a physiologically acceptable ester or salt, such as in combination with a physiologically acceptable cation or anion, as described herein above and is well known in the art.

A pharmaceutical composition of the invention may be prepared, packaged, or sold as a free-flowing powder, a tablet, a capsule, a lozenge, a liquid, a liquid concentrate or a syrup.

In some embodiments, the pharmaceutical composition prepared, packaged, or sold in bulk, as a single unit dose, or as a plurality of single unit doses. In preferred embodiments, the composition is a unit dosage form composition.

As used herein, a "unit dosage form" is a discrete amount of the pharmaceutical composition comprising a predetermined amount of the active ingredient, herein a binge regulating agent represented by Formula I as described herein. The amount of the active ingredient is generally equal to the dosage of the active ingredient which would be administered to a subject, or a convenient fraction of such a dosage such as, for example, one-half or one-third of such a dosage.

Controlled- or sustained-release formulations of a pharmaceutical composition described herein may be made using conventional technology.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A formulation of a pharmaceutical composition suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Dispersing agents include, but are not limited to, potato starch and sodium starch glycollate. Surface active agents include, but are not limited to, sodium lauryl sulphate. Diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets.

Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Lactulose can also be used as a freely erodible filler and is useful when the binge regulator are prepared in capsule form.

Liquid formulations of a binge regulator, which are suitable for oral administration may be prepared, packaged, and sold either in liquid form or in the form of a dry product intended for reconstitution with water, an alcoholic beverage or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively).

Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

In some embodiments, a preparation comprising the binge mitigation agent is in the form of a syrup or elixir or for administration in the form of drops, and may comprise active ingredients optionally together with a sweetener, which is preferably calorie-free, and which may further include methylparaben or propylparaben as antiseptics, a flavoring and a suitable color.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition described herein may comprise each of the components described herein above with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a binge regulating agent described herein may be prepared using known methods. Such formulations may be used, for example, to form tablets, to fill capsules, or to prepare an aqueous or oily suspension or solution by addition of an aqueous or oily vehicle thereto. Each of these formulations may further comprise one or more of a dispersing or wetting agent, a suspending agent, and a preservative as described herein. Additional excipients, such as fillers and sweetening, flavoring, or coloring agents, may also be included in these formulations.

A pharmaceutical composition comprising at least one binge mitigation agent as described herein may be prepared, packaged, or sold in a formulation suitable for buccal administration. Such formulations may, for example, be in the form of tablets or lozenges made using conventional methods, and may, for example, comprise about 0.1% to about 20% (w/w) active ingredient, the balance comprising an orally dissolvable or degradable composition and, optionally, one or more of the additional ingredients described herein. Alternatively, formulations suitable for buccal administration may comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and may further comprise one or more of the additional ingredients described herein.

A pharmaceutical composition comprising at least one anti bingeing agent may be prepared, packaged, or sold in a formulation suitable for intramucosal administration. Intramucosal administration of binge mitigators allows passage or absorption of the active agents across mucosa. Such type of administration is useful for absorption orally (gingival, sublingual, buccal, etc.), rectally, vaginally, pulmonary, nasally, etc.

In some embodiments, the pharmaceutical composition described herein is applied via sublingual administration. This route of administration is capable of producing a rapid onset of action due to the considerable permeability and vascularization of the buccal mucosa. Moreover, sublingual administration can also allow the administration of active ingredients, in cases where they are not normally absorbed at the level of the stomach mucosa or digestive mucosa after oral administration, or alternatively in cases where they are partially or completely degraded in acidic medium after ingestion of, for example, a tablet.

Sublingual tablets are usually prepared by direct compression of a mixture of powders comprising the active ingredient and excipients for compression, such as diluents, binders, disintegrating agents and adjuvants. In an alternative method of preparation, the active ingredient and the compression excipients can be dry- or wet-granulated beforehand.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The phrases "flavoring agent" and "odoriferous agent", as used herein, describe a class of substances which are added to edible products in order to induce a certain flavor or smell in the product, and are commonly referred to also as "flavorants". Flavorants can be synthetic or natural extracts, which are extracted from a source substance. Typical flavorants are specific and often complex mixtures of singular naturally occurring or synthetic flavor compounds combined together to either imitate or enhance a natural flavor. Many flavorants are esters, which can be characterized by a typical flavor, such as, for some non-limiting examples, diacetyl which gives a buttery flavor, isoamyl acetate that is perceived as banana, cinnamic aldehyde which is the basis for the typical flavor of cinnamon, ethyl propionate is perceived as fruity, limonene is perceived as orange, ethyl-(E, Z)-2,4-decadienoate is perceived as pear, allyl hexanoate is perceived as pineapple, ethyl maltol, is perceived as sugar or cotton candy, methyl salicylate is known as the wintergreen flavor, and benzaldehyde is perceived as bitter almond.

In some embodiments, the flavoring agent used is of a natural source and can be, for example, an extract of a fruit, a vegetable, a herb or of any other edible substance, a fruit juice or a vegetable juice, or any combination thereof. Such natural flavoring agents are often considered also as providing an added nutritional value to an alcohol-substitute beverage containing same.

The terms "color agent" or "colorant", as used herein, refers to any natural or synthetic coloring substance, and describes any substance that is added to food or drink in order to alter its color. Exemplary usable colorants include, but are not limited to, synthetic colorants such as FD&C Blue No. 1—Brilliant Blue FCF (E133), FD&C Blue No. 2—Indigotine (E132), FD&C Green No. 3—Fast Green FCF (E143), FD&C Red No. 40—Allura Red AC (E129), FD&C Red No. 3—erythrosine (E127), FD&C Yellow No. 5—tartrazine (E102), and FD&C Yellow No. 6—Sunset Yellow FCF (E110), and natural food colorants such as carmine (E120), enocianin (E163), black carrot (E163), paprika (E160c), annatto (E160b), beta carotene (E160a), lutein (E161b), riboflavin (E101), curcumin (E100), copper chlorophyllin (E141), chlorophyll (E140), caramel (E150), and extracts of foodstuffs such as elderberry, aronia, grape, beetroot, carrot, turmeric (tumeric) root, spinach, stinging nettle and burnt sugar (caramelized sugar).

The term "preservative", as used herein, describes a synthetic or natural additive substance that is added to edible products in order to prevent or retard chemical and biochemical decomposition of the product by oxygen, moisture and/or microbes. Exemplary anti-microbial preservatives include, but are not limited to, calcium propionate, sodium nitrate, sodium nitrite, sulfites (sulfur dioxide, sodium bisulfite, potassium hydrogen sulfite, etc.) and disodium EDTA, sodium benzoate, potassium sorbate. Natural substances that retard microorganisms growth include lactic acid, salt, sugar and vinegar.

Exemplary antioxidant preservatives include, but are not limited to, butylated hydroxyanisole (BHA) and butylated hydroxytoluene (BHT). Natural antioxidants include, but are not limited to, herbal extracts such as rosemary and oregano, and vitamins such as Vitamin E and Vitamin C (ascorbic acid).

The phrase "foaming agent", as used herein, describes an edible surfactant, which when present in small amounts, facilitates the formation of a foam, or enhances its colloidal stability by inhibiting the coalescence of bubbles. Exemplary foaming agents include, without limitation, sodium laureth/lauryl sulfate (SLS), sodium lauryl ether sulfate (SLES) and ammonium lauryl sulfate (ALS).

The phrase "antifoaming agent", as used herein, describes an edible substance that inhibits the formation of foam and curbs effusion or effervescence in edible products. An exemplary antifoaming agent is polydimethylsiloxane.

The phrases "viscosity modifying agent" or "thickener" as used herein are interchangeable and describe agents that enables to control the viscosity of the beverages described herein. Exemplary thickeners include, but are not limited to, starch-based thickeners such as maltodextrin and gum-based thickeners such as xanthan or cellulose gum.

It is expected that during the life of a patent maturing from this application many relevant binge behaviors and binge regulators (other than the aminoindan derivatives described herein) will be developed and the scope of the terms "binge" and "binge regulator" is intended to include all such new technologies a priori. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 or 1 to 8 carbon atoms. Most preferably, unless otherwise indicated, the alkyl is a lower alkyl having 1 to 8 carbon atoms.

An "alkenyl" group refers to a partially unsaturated hydrocarbon including straight chain and branched chain groups, which consists of at least two carbon atoms and at least one carbon-carbon double bond. Preferably, the alkenyl is a medium size alkenyl having 2 to 10 or 2 to 8 carbon atoms. Most preferably, unless otherwise indicated, the alkenyl is a lower alkenyl having 2 to 4 carbon atoms. Non-limiting examples of alkenyl include ethenyl (vinyl), propenyl, butenyl, pentenyl and hexenyl.

An "alkynyl" group refers to an a partially unsaturated hydrocarbon including straight chain and branched chain groups, which consists of at least two carbon atoms and at least one carbon-carbon triple bond. Preferably, the alkynyl is a medium size alkynyl having 2 to 10 or 2 to 8 carbon atoms. Most preferably, unless otherwise indicated, the alkynyl is a lower alkynyl having 2 to 8 carbon atoms. Non-limiting examples of alkynyl include ethynyl, propynyl, butynyl, pentynyl and hexynyl.

A "cycloalkyl" group refers to a saturated, all-carbon monocyclic or polycyclic (fused ring, i.e., rings which share an adjacent pair of carbon atoms) group, having 3 to 20, preferably 3 to 8 carbon atoms. Examples, without limitation, of cycloalkyl groups are cyclopropane, cyclobutane, cyclopentane, cyclohexane and cycloheptane.

An "aryl" group refers to an all-carbon monocyclic or polycyclic (fused-ring i.e., rings which share adjacent pairs of carbon atoms) groups having a completely conjugated pi-electron system. Examples, without limitation, of aryl groups are phenyl, naphthalenyl and anthracenyl.

A "heteroaryl" group, as used herein, refers to a monocyclic or polycyclic (fused ring, i.e., rings which share an adjacent pair of atoms) group having in the ring(s) one or more heteroatoms, selected from nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline, phthalimide, and purine.

A "heteroalicyclic" group as used herein refers to a monocyclic or polycyclic (namely, a fused ring group as defined herein) having in the ring(s) one or more atoms such as nitrogen, oxygen and sulfur. The rings may also have one or more double bonds. However, the rings do not have a completely conjugated pi-electron system. Representative examples are piperidine, piperazine, tetrahydro furane, tetrahydropyrane, morpholino, pyrroline and the like.

As used herein, the term "hydroxyalkyl" refers to an alkyl, as this term is defined herein, substituted by an OH group, and includes, for example, hydroxymethyl, hydroxyethyl, hydroxypropyl and hydroxy-n-butyl.

As used herein the term thienyl refers to the radical:

As used herein, the term "halogen", which is also referred to herein interchangeably as "halo", includes chloro (Cl), bromo (Br), iodo (I) and fluoro (F).

Any of the alkyl, alkenyl, alkynyl, cycloalkyl, heteroaryl, heteroclicylic or aryl group as defined herein may be substituted or unsubstituted. When substituted, the substituent group can be, for example, alkyl, —O—($C_1$-$C_8$)alkyl, —O—($C_3$-$C_8$)cycloalkyl, trihaloalkyl, hydroxyalkyl, ($C_3$-$C_8$) cycloalkyl, alkenyl, alkynyl, aryl, heteroaryl, heteroalicyclic, halo, OH, O-aryl, —SH, —S—($C_1$-$C_8$)alkyl, —S—($C_3$-$C_8$)cycloalkyl, —S-aryl, —O—S=O, —S(=O)$_2$—R', —CN, —NO$_2$, —O—P(=O)(OR')(OR''), —PR'R'', —C(=O)—R', —C(=S)—R', —C(=O)—O—R', —C(=S)—O—R', —OC(=O)—NR'R'', —OC(=S)—NR'R'', —OC(=S)—NR'R'', —S(=O)$_2$—NR'R'', and —NR'R'', where R' and R'', each independently, is hydrogen, alkyl, alkenyl, cycloalkyl, aryl, heteroaryl (bonded through a ring carbon) or heteroalicyclic (bonded through a ring carbon), as these terms are defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Regulating Binge Drinking During a Drinking Session

Unit dosage forms each comprising 80 mg of Compound 1 and/or Compound 2 as described herein, in gelatin capsules (size "1), are prepared.

A capsule is swallowed at the beginning of a drinking session with each alcoholic drink. Volunteers are asked about their drinking habits at both the beginning and end of a drinking session. At the end of the session they are also asked if their alcohol consumption changed due to the consumption of the binge mitigating agent. Then, the volunteers are asked if they would repeat the process of their own free will if the mitigating agent was readily accessible (for example, sold with alcohol or as a pill over the counter).

In an exemplary study, volunteers reported a substantial reduction (e.g., of at least 30%) in alcohol consumption during the drinking session.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of regulating binge behavior, the method comprising administrating to a subject in need thereof a compound represented by Formula I:

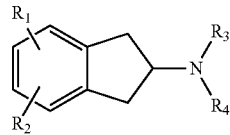

Formula I wherein:
each of $R_1$ and $R_2$ is independently selected from the group consisting of H, ($C_1$-$C_8$)alkyl, ($C_2$-$C_4$)alkenyl, ($C_2$-$C_8$)alkynyl, ($C_3$-$C_8$)cycloalkyl, aryl, heteroaryl, heteroalicyclic, —O($C_1$-$C_6$)alkyl, OH, —OS(=O)$_2$CF$_3$, —OS(=O)$_2$—($C_1$-$C_6$)alkyl, —S(=O)R$_5$, —CO$_2$R$_5$, —CONR$_5$R$_6$, —COR$_5$, —CF$_3$, CN, —SR$_5$, —SO$_2$NR$_5$R$_6$, —SO$_2$R$_5$, —OCO—($C_1$-$C_6$)alkyl, —NCO—($C_1$-$C_6$)alkyl, —CH$_2$O—($C_1$-$C_6$)alkyl, —($C_1$-$C_6$)alkyl-OH, and halogen, or, alternatively, $R_1$ and $R_2$ together with two or more of the phenyl carbon atoms form a $X_1$—(CR$_5$R$_6$)$_m$—$X_2$— ring, wherein each of $X_1$ and $X_2$ is independently selected from O, NH or S and m is 1, 2, 3, or 4;

each of $R_3$ and $R_4$ is independently selected from the group consisting of H, ($C_1$-$C_8$)alkyl, ($C_2$-$C_8$)alkenyl, ($C_2$-$C_8$)alkynyl, ($C_3$-$C_8$) cycloalkyl, and —(CH$_2$)$_p$-thienyl, wherein p is 1, 2, 3, or 4, or alternatively, $R_3$ and $R_4$ are joined together to form a heterocylic ring (heteroalicyclic or heteroaryl) containing the nitrogen atom to which they are attached; and each of $R_5$ and $R_6$ is independently selected from the group consisting of H, ($C_1$-$C_8$)alkyl, ($C_2$-$C_8$)alkenyl, ($C_3$-$C_8$)cycloalkyl and aryl, thereby regulating the binge behavior, wherein at least one of $R_3$ and $R_4$ is H, and wherein the compound of Formula I is selected from:

5-methoxy-2-aminoindan;
5,6-dimethoxy-2-aminoindan;
5-methoxy-2-(N-propylamino)indan;
5,6-dimethoxy-2-(N-propylamino)indan; 5-(trifluoromethylsulfonyloxy)-2-(N-propylamino)indan;
5,6-(di-trifluoromethylsulfonyloxy)-2-(N-propylamino) Indan; and
5,6-dimethoxy-2(pyrrolidino)indan.

2. The method of claim 1, wherein said binge behavior is associated with alcohol consumption, eating, tobacco consumption, shopping or sexual conduct.

3. The method of claim 2, wherein said binge behavior is binge drinking.

4. The method of claim 1, wherein said compound forms a part of a composition, which further comprises a pharmaceutically acceptable carrier.

5. The method of claim 4, wherein said composition is in a form of a free-flowing powder, a tablet, a capsule, a lozenge, a liquid, a liquid concentrate or a syrup.

6. The method of claim 4, wherein said composition is a unit dosage form composition.

7. The method of claim 6, wherein an amount of said compound in said unit dosage form ranges from 30 mg to 130 mg.

8. The method of claim 7, wherein said amount of said compound is 70 mg.

9. The method of claim 1, wherein said compound or composition is administered to a subject orally.

10. The method of claim 1, wherein the compound of Formula I is 5-methoxy-2-aminoindan.

11. A pharmaceutical composition comprising 5-methoxy-2-aminoindan,
    the composition being formulated for oral administration, and being a liquid unit dosage form composition.

12. The pharmaceutical composition of claim 11, being packaged as a single unit dose or as a plurality of single unit doses.

13. The pharmaceutical composition of claim 11, wherein said unit dosage form comprises from 30 mg to 130 mg of said compound.

\* \* \* \* \*